US005580791A

United States Patent [19]

Thorpe et al.

[11] Patent Number: 5,580,791

[45] **Date of Patent: *Dec. 3, 1996**

[54] ASSAY OF WATER POLLUTANTS

[75] Inventors: Gary H. G. H. Thorpe, Handsworth; Thomas P. Whitehead, Leamington Spa, both of England

[73] Assignee: British Technology Group Limited, London, England

[ * ] Notice: The term of this patent shall not extend beyond the expiration date of Pat. No. 5,395,755.

[21] Appl. No.: 449,249

[22] Filed: May 24, 1995

Related U.S. Application Data

[63] Continuation of Ser. No. 94,075, filed as PCT/GB92/00157 Jan. 28, 1992, abandoned.

[30] Foreign Application Priority Data

Jan. 29, 1991 [GB] United Kingdom .................. 9101928
Oct. 3, 1991 [GB] United Kingdom .................. 9121082

[51] Int. Cl.[6] .................................................. G01N 33/18

[52] U.S. Cl. .............................. 436/62; 436/172; 436/39; 435/4

[58] Field of Search ............................... 436/62, 66, 826, 436/172, 800, 39; 435/28, 4, 7; 422/52; 544/234, 237

[56] References Cited

U.S. PATENT DOCUMENTS

| | | | |
|---|---|---|---|
| 3,359,973 | 12/1967 | Hoffman | 435/291 |
| 4,643,835 | 2/1987 | Koeplin-Gall et al. | 210/754 |
| 4,729,950 | 3/1988 | Kricka et al. | 435/28 |
| 4,835,101 | 5/1989 | Kao et al. | 435/28 |
| 5,043,266 | 8/1991 | Dewar et al. | 435/7.9 |
| 5,055,397 | 10/1991 | Michaels et al. | 435/9 |
| 5,116,759 | 5/1992 | Klainer | 435/288 |
| 5,209,934 | 5/1993 | Ekis, Jr. et al. | 424/661 |

FOREIGN PATENT DOCUMENTS

| | | |
|---|---|---|
| 0116454 | 8/1984 | European Pat. Off. . |
| 1542155 | 3/1979 | United Kingdom . |

OTHER PUBLICATIONS

Bulich, chapter 4 "Bioluminescence Assays" vol. 1, 57–74 (1986).

J. K. Wong et al. "Quenching of peroxidized luminol . . . " Photochemistry & Photobiology, vol. 33 (1981), PP. 737–740.

P. S. Rao et al. "Specificity of oxygen radical scavenger . . . " Biochemical & Biophysical Research Communications, vol. 150 No. 1 (Jan. 15, 1988), 38–44.

Analytical Letters, 81(B13), 1579–1592 (1985) Frew et al "Assay of Some Clinically Important Reductants by a chemiluminescence–Delay Technique".

J. of Chemical Education, vol. 64 No. 1, Jan. 1987 pp. 70–71 Ackerson, Tested Demonstrations "Demonstrations of Condensation–Vaporization".

Clin. Chem. 25/9, 1531–1546 (1979) Whitehead et al "Analytical Luminescence: Its Potential in the Clinical Laboratory".

LKB Wallac Luminescence Reagents Catalogue (early 1986) pp. 3–8.

Methods of Bioluminescence Analysis, Boehringer Mannheim Bioluminescence Chemiluminescence.

*Primary Examiner*—James C. Housel
*Assistant Examiner*—Rachel Heather Freed
*Attorney, Agent, or Firm*—Nixon & Vanderhye

[57] ABSTRACT

A method of assay of antioxidant activity of a sample of water, which comprises monitoring the change exerted by the sample on a luminescent reaction.

14 Claims, 4 Drawing Sheets

ASSAY OF WATER POLLUTANTS

This is a Rule 62 continuation of application Ser. No. 08/094,075, filed as PCT/GB92/00157 Jan. 28, 1992, now abandoned.

BACKGROUND OF THE INVENTION

1. Field of Invention

This invention relates to a method of assay of water to determine an aspect of its biological and chemical quality, using a luminescent reaction.

2. Description of Prior Art

Pollution is an endemic problem In water throughout the world. Many tests exist to detect pollutants in water. Generally pollutants have the effect of decreasing the oxygen availability within the water. Such oxygen deprivation may be detrimental to the extent of disrupting the delicate ecosystem within the source of water. In rivers, ponds, lakes and the like this can result in the death of both plantlife and wildlife as the levels of pollutants increase and correspondingly the amount of oxygen in the water decreases.

The oxygen levels in a sample of water indicates the amounts or presence of pollutants. Several methods exist for measuring oxygen in water. The Winkler titration is a preferred method for measuring dissolved oxygen. More sophisticated methods involve the use of oxygen electrodes. Of wider use in the monitoring of pollution has been the biochemical oxygen demand (BOD) test. In it the decrease In dissolved oxygen concentration resulting primarily from biological action (bacterial oxidation) is measured over a period of 5 days at 20° C. The BOD test suffers from several drawbacks. It fails to mimic the natural processes occurring in the water—this is primarily due to the test being carried out in the dark. It can also be complicated by lack of suitable bacteria in the sample, or the presence of toxic compounds that prevent the breakdown of pollutants. Additionally, the oxygen content of the sample may change during storage. Generally, many considerations have to be taken into account to obtain a true value. Results have a high degree of variability. These and other related methods are discussed in Standard Methods for the Measurement of Water and Waste Water, 15th edition, Amer. Pub. Health Assoc. 1979.

Recently, the National Rivers Authority have recommended that the current 5 day BOD test be replaced by measuring Total Organic Carbon (TOC) (Laboratory Equipment Digest, August 1991, 41–42). This method also has several drawbacks. It involves UV radiation and the use of concentrated nitric acid, requiring special laboratory conditions. Inorganic carbonates, bicarbonates and carbon dioxide present in the water interfere with the reaction and must first be removed—hence the end result is often inaccurate.

These methods supply only limited information, are lengthy and require specialised laboratory apparatus and technicians.

There is therefore a need for a rapidly functioning method of assessing the biological and chemical quality of a water sample, which can be carried out simply and on site.

Further prior art is mentioned after the "Summary of the Invention", without which its context would not be clear.

SUMMARY OF THE INVENTION

It has now been found that when a test sample of water is added to a chemiluminescent reaction, the antioxidants and other pollutants present cause a transient reduction in the observed luminescence (measured light output). After a short period the level of luminescence recovers somewhat. Thus, from the change in luminescence, the antioxidant capacity of a given water sample can be assayed (determined) utilising a luminescent reaction, providing an indication of the biological and chemical quality of the water sample. The presence of pollutants, toxic chemicals and the like will increase the antioxidant capacity of the sample, whereas pure water will have a lower antioxidant capacity.

The invention provides a method of assay of the antioxidant capacity of a sample of water which comprises monitoring the change exerted by the sample on a luminescent reaction.

The term "assay" or "determination" as used herein, includes qualitative, semi-quantitative and quantitative indications, assessments, estimations and measurements.

In a first embodiment, the sample is added before the initiation of the reaction and at a pre-determined time after such initiation, preferably 2 minutes after, the level of luminescence produced by the test reaction is measured and compared to a similar measurement taken from a control reaction having no test sample of water added. The difference between these values provides an index as to the antioxidant capacity of the sample.

Alternatively, the time period from the initiation of the reaction until the level of luminescence is observed to be at a substantially constant rate may be measured.

The term "antioxidant capacity" is herein used to refer to a measure of the biological and chemical quality of the water, and is believed to be an important factor in the assessment of water quality. It has been shown to correlate well with TOC and BOP values, but is a more rapidly obtainable and sensitive measurement.

In a further aspect of the first embodiment, a test sample of water is added to a progressing luminescent reaction, i.e. after the reaction has been initiated. The antioxidants and pollutants present cause a transient reduction in the observed luminescence (measured light output). The time period, during which the observed luminescence is reduced, provides an index of the antioxidant capacity of the test sample.

Preferably, the water sample is added to the progressing luminescent reaction when the level of luminescence is substantially constant, that is the level of luminescence after rising to a maximum level, plateaus, remaining at substantially the maximum level or decreasing at a moderate rate, typically of up to 0.6% per minute. It will be appreciated that the nature of this plateau can vary considerably according to the reactants chosen, but one skilled in the art will have no difficulty in recognising a plateau since such luminescent reactions are known per se.

Preferably, the water sample is added to the progressing luminescent reaction before it reaches the said substantially constant level, but is within 10% of the maximum.

The addition of the water sample to the progressing luminescent reaction results in a sudden drop in the level of luminescence, which is followed by a recovery towards the said substantially constant level. The time interval between the time when the sample is added and a predetermined level of recovery is measured and provides an index of the antioxidant capacity of the sample. The level of lumtnescence recovers to a second substantially constant level. This second level may be lower than the original said substantially constant level. The level of recovery of luminescence at a given time interval from the time when the sample is added can be measured and compared to the level of luminescence at the time when the sample was added or compared to the level of luminescence in the control at the same time. As is discussed hereinafter, assays can be based on other time periods during the reaction.

Occasionally, a pollutant may be present in a sample that inactivates an enzyme used in the luminescent reaction resulting in partial or complete inhibition of light emission.

Advantages of the present invention include the following: 1) the assay can be carried out in a single step for each sample, i.e. there is no series of separate reactions required to obtain the result; 2) several aspects of the assay comprise a "real time" measurement which enables the level of observed luminescence before the addition of the test sample to be compared with the level observed after the transient depression; the comparison of the levels of luminescence and/or the shape of the curve defining the transient depression provides further information regarding the nature of the antioxidants present in the test sample, and 3) the apparatus required is relatively simple, easy to maintain and permits several assays to be carried out simultaneously.

The invention is of foremost applicability to oxygen-dependent chemiluminescent reactions, especially peroxidase-catalysed and especially such reactions which will provide a high and substantially constant rate of photon production or level of light output as described hereinbefore. To meet such a requirement, an enhancer of the luminescent reaction will often be required.

In a further embodiment of the invention, the antioxidant contribution of any specific or particular classes of antioxidants known or suspected to be present in a sample may be determined by comparing the antioxidant capacity of the sample before and after removal of that specific antioxidant. Furthermore, the pattern of luminescence output may itself provide information as to the class of pollutants present in the sample.

The invention also includes a kit for carrying out the assay comprising a luminescent substrate and an antioxidant (for carrying out standardisations). Where the luminescent reaction is enzyme-catalysed, the term "luminescent substrate" is used to refer to the chemical species starting material which undergoes a chemical change in the reaction rather than to the enzyme substrate. Thus, in the case of reaction of luminol with a peroxide and peroxidase, the luminescent substrate is luminol, not peroxide. Other reagents required or desirable for the luminescent reaction can, of course, be included in such a kit.

Description of Additional Prior Art

It is a known feature of antioxidants that they will depress luminescence observed from a number of different chemiluminescent sources (Radi et al, Biochimica et Biophysica Acta (1989), 994, 89–93). This property has been used in an attempt to determine which radicals are preferably "mopped up" by which antioxidant (Rao et al, Biochem. and Biophys. Res. Commun. (1988), 150, (1), 39–44) and also to compare the efficiency of different food antioxidants (Kahl et al, Arch. Toxicol. (1987), 60, 158–162). It has further been developed to assay superoxide dismutase (see Popov et al., Biomed. Biochim. Acta (1987), 46, (11), 775–9). Frew et al. (Anal. Lett. (1985) 18 (B 13) 1579–1592) have developed a chemiluminescent delay technique for the assay of reductants. All the components for the ferrihaem-catalysed oxidation of luminol were mixed together with the reductant before the addition of hydrogen peroxide which initiated the chemiluminescent reaction. The time delay before any chemiluminescence was observed was taken as an index of the amount of reductant originally added. This relationship between the time delay and concentration of reductant was linear over a limited range of reductant concentrations. Wong et al. (Photochem. & Photobiol. (1981) 33 737–740) found a linear relationship between time delay before observation of chemiluminescence and concentration of reduced pyridine nucleotides, for example NADH and NADPH. They used a luminol-HRP unenhanced chemiluminescent reaction, and mixed the reduced nucleotides with the reactants before the initiation of the reaction by hydrogen peroxide. They also observed that the maximum level of light output was reduced when higher concentrations of reduced nucleotides were added. This quenching of light output was also observed when using other reductants such as ascorbic acid, dithionite, ferrocyanide and cysteine. Neither of these two last-mentioned papers discuss further experimentation or investigation of the observed phenomena and no further applications of these observations were proposed.

In all these prior references there has been no suggestion of using a chemiluminescent method for assaying water quality.

BRIEF DESCRIPTION OF THE ACCOMPANYING DRAWINGS

DESCRIPTION OF THE PREFERRED EMBODIMENTS

Figure 1:
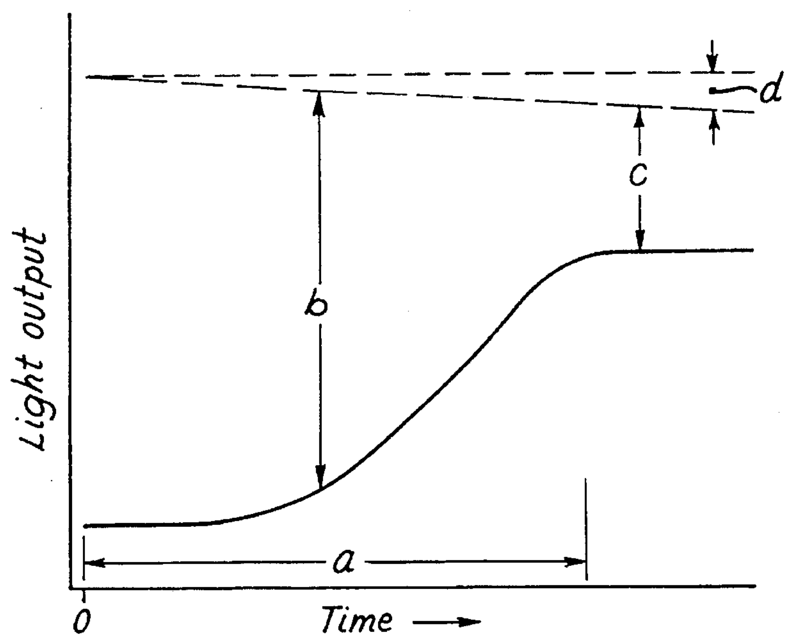
FIGS. 1–5 are graphs of light emission from a luminescent reaction, to which different samples have been added, plotted against time.
Figure 2:
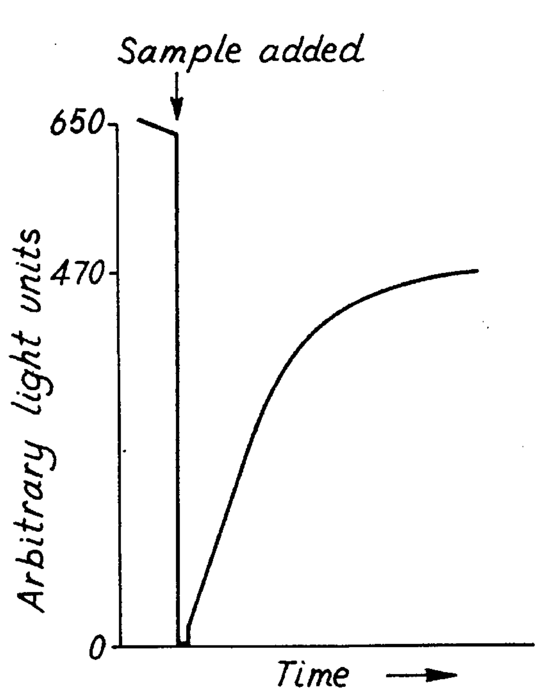
Figure 3:
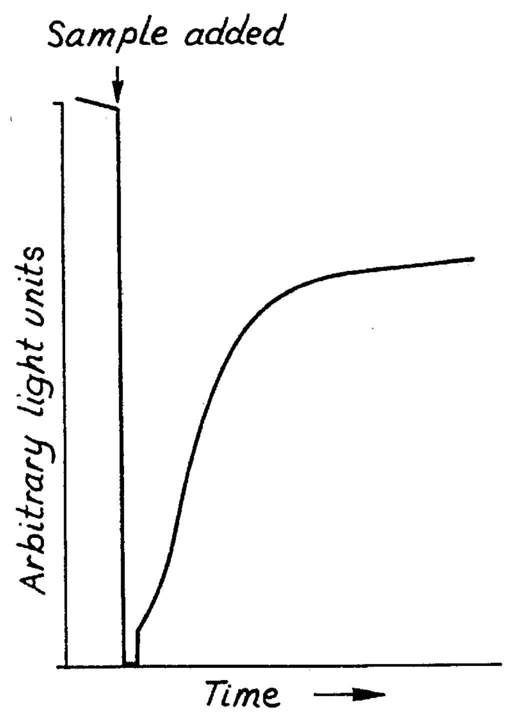
Figure 4:
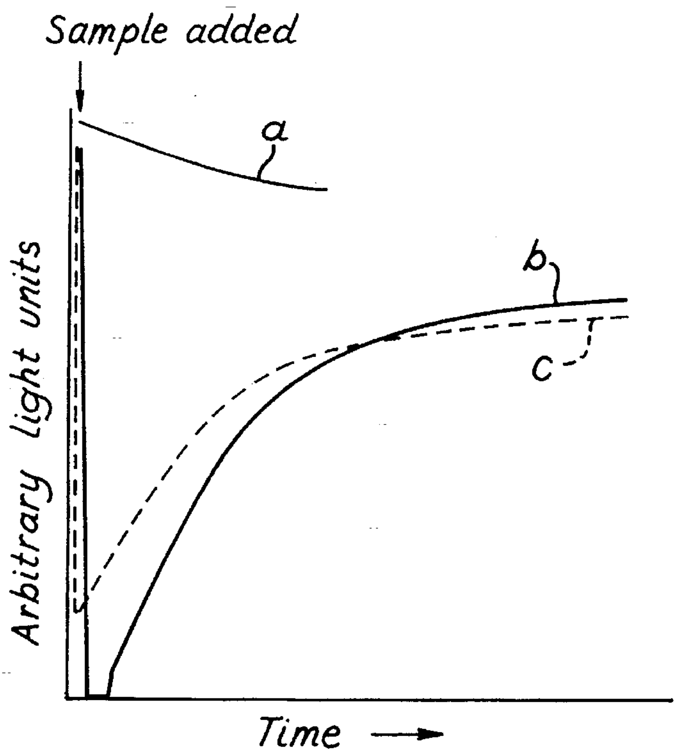

The oxygen-providing component of the luminescent reaction need not be molecular oxygen but can be hydrogen peroxide or a perborate, for example.

One suitable chemiluminescent reaction which exhibits a relatively constant photon emission is one in which the reaction takes place between a peroxidase, an oxidant and a dihydrophthalazinedione (DPD), In the presence of an enhancer. Such chemiluminescent reactions are described in our European Patents Nos. 87,959 and 116,454 and in U.K. Patent 2162946 and U.K. Patent Application No. 8814148.6 (Publication No. 2205945A) and any of these can be used In the context of the present invention.

For the purposes of the present invention a preferred DPD Is luminol or isoluminol, a preferred oxidant is hydrogen peroxide or sodium perborate and preferred enhancers are para-iodophenol, para-hydroxy cinnamic acid or para-imidazol-1-ylphenol, most preferably para-iodophenol. These enhancers give a high and relatively constant rate of light emission over an extended period and may be used as a "benchmark" of preferred maximum levels of high output for use in the context of the invention, regardless of the nature of the enhancer or other reagents employed. Other enhancers that are of use in the present invention include 2-cyano-6-hydroxybenzothiazole, 1-bromo-2-naphthol, para-phenyl- phenol and N,N,N',N'-tetramethylbenzidine. A preferred peroxidase enzyme is horseradish peroxidase (HRP).

The chemiluminescent reactions described above are intended only to be representative of the many suitable luminescent reactions that may be known to those skilled in the art. Many other known chemiluminescent reactions or variations thereof are likely to be found useful for the present purposes and can be investigated by simple experimentation.

The changes in light emission may be monitored using a conventional photomultiplier tube luminometer with a recorder. For simple qualitative studies a photographic film or even visual observation may be suitable. A further advantage of the present Invention is that because of the relatively high intensity of light emission the assay may be monitored using a "hand held" battery-operated luminometer from which readings of photon output can be made every 30 seconds or less.

The assay used in the present invention is of use with many different types of water. Thus, it is applicable to sewage (treated or untreated), river, sea water, reservoir, tap, industrial waste water, silage, cattle slurry and dairy washings.

In a further embodiment, the invention can be used to determine the contribution of specific or particular classes of antioxidants Known or suspected to be present in a water sample, by comparing the antioxidant capacity as measured by the method of the invention before and after the specific or particular classes of antioxidants have been removed or extracted.

Thus, the antioxidant contribution of substances such as proteins contained within a water sample may be determined by comparing the antioxidant capacity of the sample before and after the proteins have been removed. Protein removal may be achieved by methods well known in the art including precipitation or filtration with or without centrifugation through a molecular filter.

Similarly, the antioxidant contribution of other antioxidants may be determined using methods Known in the art to remove them from the sample, for example using ion-exchange filtration to remove heavy metals, anions or cations and phenols may be removed by boiling. A further application of the invention is in the identification of the source of pollution in a river or reservoir and the like. An example of such a use is given in Example 2 where, by progressively measuring the antioxidant capacity of samples taken upstream of a polluted pond, the origin of the pollutants was correctly identified.

The assay is sensitive to detect pollutants present in typical concentrations. Sensitivity depends on the concentration of antioxidants present in the sample. Thus, in less concentrated samples, e.g. river water or tap water, much larger quantities are required, perhaps 20–50 times as much as for raw sewage. In heavily polluted samples such as cattle slurry or silage, samples may require dilution by up to 10,000 to 20,000 times. Conveniently, a tap water sample merely replaces the distilled water used to dilute the reagents giving the luminescent signal. When sea water is being tested it is essential that an artificial sea water or saline is used in the "control" reaction.

The assay is sensitive to a wide range of pollutants, thus it has been shown that the following compounds have an effect on the level of light output:

Resorcinol, catechin, captopril, N,N,N',N'-tetramethylbenzidine, vanillic acid, o-phenylenediamine, p-phenylenediamine, chromium chloride, potassium ferrocyanide, sodium thiosulphate, dimethyl sulphoxide, 4-methoxybiphenyl, catalase, dipyridamole, phenol, m-chlorophenol, ethanol, diethylthiocarbamic acid, butylated hydroxytoluene, gallic acid, N-2-mercaptopropionyl glycine, reduced glutathione, albumin, bilirubin and cysteine.

Each of these compounds has been observed to effect light output in a manner similar to the graphs shown in FIGS. 2–5.

This list is by no means exhaustive. As can be seen, polyphenols, substituted amines and sulfhydryl containing compounds all affect light output. These classes of compounds are good examples of the type of pollutants frequently found in water.

To obtain a quantitative value as to the antioxidant capacity the measured parameter can be compared to a "standard" value. A suitable standard may be selected from the list above, but is preferably TROLOX (6-hydroxy-2,5,7,8-tetramethylchroman-2-carboxylic acid) or o-phenylenediamine.

FIG. 1 of the drawings illustrates how the light intensity of the luminescent reaction can be affected by addition of sample prior to the initiation of the reaction at time zero, (bold line) as compared to a control luminescent reaction with no water sample (dashed line), light intensity being plotted against time. Referring to FIG. 1, the distances marked have the following meanings:

(a) is the time between the initiation of the luminescence reaction and observation of a substantially constant level of luminescence, (b) is the difference in the level of luminescence at a fixed point after the initiation of the luminescent reaction between a test sample reaction and a control reaction, (c) is the difference between the substantially constant level of luminescence observed in the test reaction and that of the control.

The fall in light intensity (d) is the natural decay In the enhanced reaction, due to HRP inactivation etc. This is typically a decrease of no more than 2%, preferably no more than 1% and most preferably no more than 0.6% a minute.

Alternatively, instead of measuring a time interval to the recovery of a relatively constant level of luminescence, it can be measured to some pre-determined level such as 10%–70% of either the initial value or of the final value. In another embodiment, the level of recovery of luminescence at a given time interval from the time when the sample is added is measured and compared to the level of luminescence at the time when the sample was added.

In the further aspect of the first embodiment of the invention, further parameters in the pattern of observed levels of luminescence may be used to obtain further information regarding the antioxidant capacity. Thus, the difference between the initial level of luminescence prior to the addition of the sample, and the level after the addition of the sample may be utilised, as may the time delay from the addition of the sample until the observation of a second substantially constant level of luminescence. When a control with no test water sample is run at the same time, the difference between control and test levels are also of use.

A particularly preferred kit for the assay of the invention comprises a DPD (e.g. luminol or isoluminol), an enhancer (e.g. iodophenol), a catalyst (e.g. peroxidase) and an antioxidant (e.g. 6-hydroxy 2,5,7,8-tetramethyl chroman-2-carboxylic acid o-phenylenediamine). Preferably the Kit further contains an oxidant (e.g. hydrogen peroxide) and buffer.

The following Examples illustrate the invention.

"AMERLITE" is a Registered Trade Mark of Amersham International PLC. "TROLOX" is also a registered Trade Mark.

EXAMPLE 1

USE OF ANTIOXIDANT ASSAY ON DIFFERENT WATER SAMPLES

"Amerlite" signal reagent was prepared as described in the manufacturer's instructions and a 1 in 10 dilution of this was used (100 μl "Amerlite" signal reagent to 900 μl distilled water), hereinafter described as the signal reagent. 60 μl of Amerlite HRP anti-IgG conjugate (as a source of HRP) was added to 20 ml of distilled water for use in the assay. 1 ml of signal reagent in water was placed in a cuvette to be used in the luminometer. 20 μl of the working HRP conjugate was added. This was placed in the luminometer for 2 minutes or until a substantially constant level of photon output was observed. When a constant level was attained, test sample was added and that moment taken as zero time. The reaction was allowed to continue for about 8 minutes. Measurements were made on a bench luminometer (with a photomultiplier).

The following samples of water were added in the volumes indicated. When a 900 μl sample was added it was used in place of the 900 μl distilled water.

i) sewage before it is sand-filtered, (40 μl);

ii) sewage after it has been sand-filtered, (40 μl);

iii) sewage (a) after it has been treated chemically, (40 μl);

(b) after a slow sand filtration, (40 μl);

(c) London tap water, (40 μl);

(iv)

(a) untreated sewage, (40 μl);

(b) ditto, diluted 1:100, (900 μl);

(c) ditto, diluted 1:1000, (900 μl);

(d) distilled water, (900 μl).

The plots obtained from (i)–(iv) are shown in FIGS. 2–5 respectively. Each figure shows the plot of light output from a chemiluminescent reaction on the ordinate (y axis) versus time on the abscissa (x axis).

Figure 5:
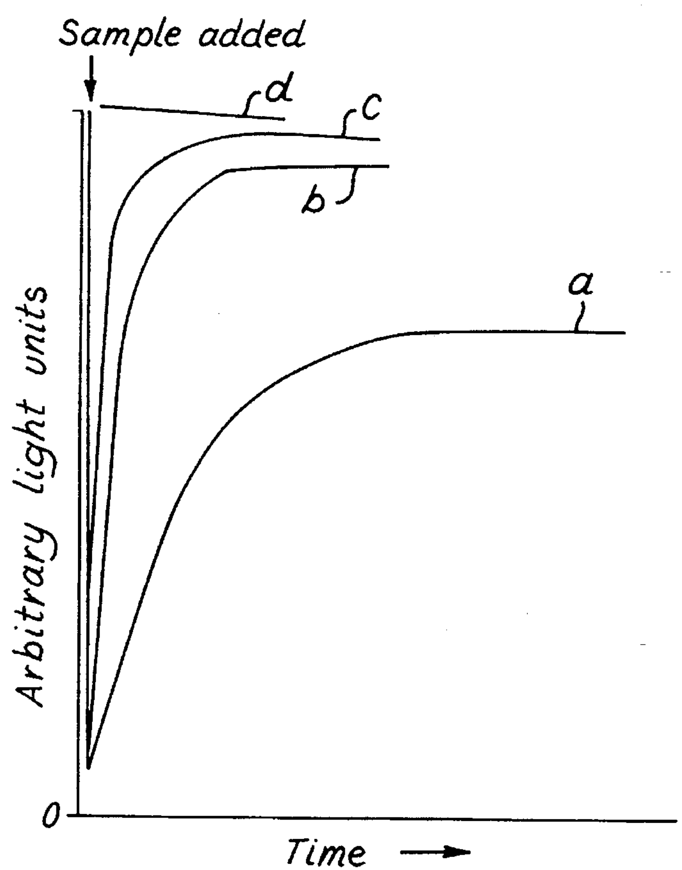

It will be seen that the more dilute the sewage the steeper the rise in luminescence to a level approaching that of potable water. In FIG. 5, (a) and (b) are not strictly comparable, since (a) relates to a 40 μl volume of sample, (b) to a 900 μl volume, thus, however, illustrating the sensitivity of the assay.

This example of the basic assay has been repeated for sea water, silage, cattle slurry and dairy washings. The last three substances have very high BOD values and had to be diluted to a very high level (1:10,000 or 1 in 20,000) to obtain a meaningful result using the present invention.

EXAMPLE 2

USE OF ASSAY IN LOCATING A SOURCE OF POLLUTION

This example describes how by using the method of the invention the source of a lake's pollution was identified. Throughout this example a hand-held luminometer was used. Reagents and quantities used were as described in Example 1. The chemiluminescent reaction was allowed to proceed for one minute after the addition of the water sample. The one minute value for a water sample was subtracted from that obtained using distilled water and the difference expressed as a % reduction of the distilled water one minute level, i.e.

$$T_1 = \frac{\underset{\text{(control)}}{Cl \text{ level after 1 minutes}} - \underset{\text{(sample)}}{Cl \text{ level after 1 minute}}}{Cl \text{ level after 1 minute (control)}} \%$$

A low $T_1$ therefore denotes little pollution.

The lake investigated was Vale Lake within the authority of the Birmingham City Engineering Department. Over the past year, the lake has shown a decline in the wildlife which it supports. When a sample of its water was assessed according to the invention, it showed a $T_1$ of 57%. A similar lake with flourishing wildlife only showed a $T_1$ of 11%. Samples were taken from the brook that supplies Vale Lake. This showed a $T_1$ of 75% using a 1 in 10 dilution of the sample. This brook was supplied by two streams. Samples were taken from both. One showed a $T_1$<10% and the other a $T_1$ of 70%. The contaminated stream was supplied by municipal surface sewers. These sewers should only have contained surface water and thus display a low $T_1$ value. Values obtained were all between 80 to 100%. With the assistance of Local District Council engineers, 5 manhole covers in streets, the sewers of which ran into the contaminated stream, were lifted and the sewers supplying the stream tested. Consistent "high" readings ($T_1$>70%) were made from the first 4 manholes until it suddenly returned to under 40% from the fifth. Examination of the sewer connections between the fourth and fifth manhole covers revealed premises where toilets and sinks had been connected to sewers intended to take only surface water, not sewerage.

The method of the present invention had thus served as a rapid method for assessing water and locating the source of water pollutants. The faulty sewer connections have been corrected and slowly the Vale Lake wildlife is reappearing.

At an inspection several months later, the brook supplying the Vale Lake had a $T_1$ of 25%. The lake itself attracts so many geese at the waters' edge that $T_1$ values of 50–70% have been recorded there. These local high $T_1$ values are due to goose waste products seeping into the water.

EXAMPLE 3

USE OF ASSAY IN ASSESSING THE "ANATOMY" OF A RIVER

This example describes how by using the method of the invention the "anatomy" of a river may be examined. By "anatomy" we mean in indication of its pollution profile relating it to supplying tributaries and other possible sources of pollution.

Conditions for performing the assays were as described above. $T_1$ values were measured in a similar manner and given in brackets.

Figure 6:
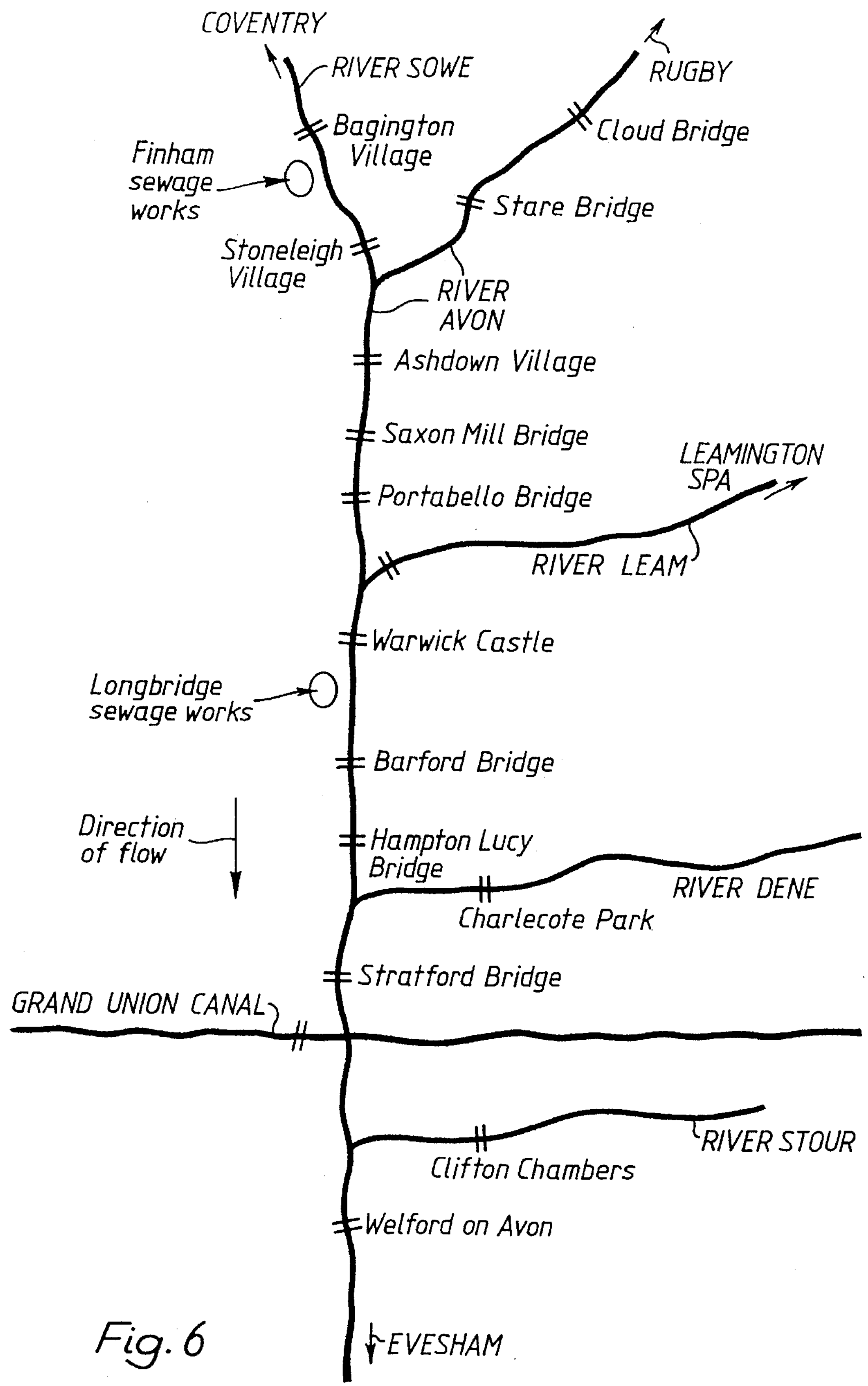
FIG. 6 is a schematic map of the River Avon.

In association with Severn Trent Water Authority, the River Avon was investigated, starting close to the City of Coventry and finishing some five miles south west of Stratford-upon-Avon at Welford-on-Avon. FIG. 6 shows a schematic map of the section of the River Avon studied.

The River Avon flows close to the large industrial town of Rugby and skirts to the east of Coventry through open country. Samples were taken at Cloud Bridge (40) and Stare Bridge (43) close to the National Agriculture Centre (NAC). At this point the river Avon is joined by the River Sowe which flows through Coventry. The river source was sampled at Baginton (57) before passing through the Finham Sewage Works which discharges treated sewage into the Sowe and this results in pollution as shown by the measurement at Stoneleigh Village (97). At Ashdown, about ½ mile down from the joining of the polluted Sowe and the Avon there is a high inhibition (91).

Readings were obtained from the Saxon Mill Bridge and the Portobello Bridge between Leamington Spa and Warwick; Saxon Mill (84) and Portabello (72). At this point the Avon is joined by the River Leam (46) and nearby downstream a reading was taken at Warwick Castle Bridge (37).

These results may be due to the natural oxidation of Finham's pollution as the Avon passes through open country without further urban pollution.

Downstream from Warwick Castle (25), treated sewage from the Warwick District Longbridge Sewage Works is discharged into the river resulting in a reading of 63 at Barford Bridge. This inhibition is further reduced some few miles further on to 52 at Hampton Lucy Bridge.

The Avon is then joined by the River Dene (66) at Charlecote Park. The Dene at this point is downstream from a small sewage plant, the flow is much less than that of the Avon. By the time the Avon reaches Stratford-upon-Avon there is no further pollution (46). The Grand Union Canal crosses the Avon a little further downstream, the canal water being clean (25).

A further tributary, the River Stow, at Clifton Chambers (55) does not appear to alter the general picture and by Welford-on-Avon (46) the Avon has values close to those upstream of the Finham pollution. Thus, using the method of the present invention a profile of a river or water source is readily obtainable and possible sources of pollution readily identifiable.

EXAMPLE 4

COMPARISON OF ANTIOXIDANT ASSAY AND TOTAL ORGANIC CARBON ASSAY (TOC)

This comparison was undertaken by the Severn Trent Water Authority using the assay of the present invention and the TOC as described in the Severn Trent Laboratories, Birmingham Laboratory, Laboratory Methods Manual.

The antioxidant assay was performed adding 200 μl of water sample to the Amerlite Signal Reagent (800 μl) prior to the initiation of the reaction by the addition of HRP (20 μl). Control reactions were performed replacing the test sample with deionised water. Both test and control reactions were allowed to proceed for 2 minutes. The difference in the levels of luminescence at two minutes between the test and control reactions was taken as an index of the antioxidant capacity of the sample, and is referred to as the $\Delta_2$ value.

Figure 7:
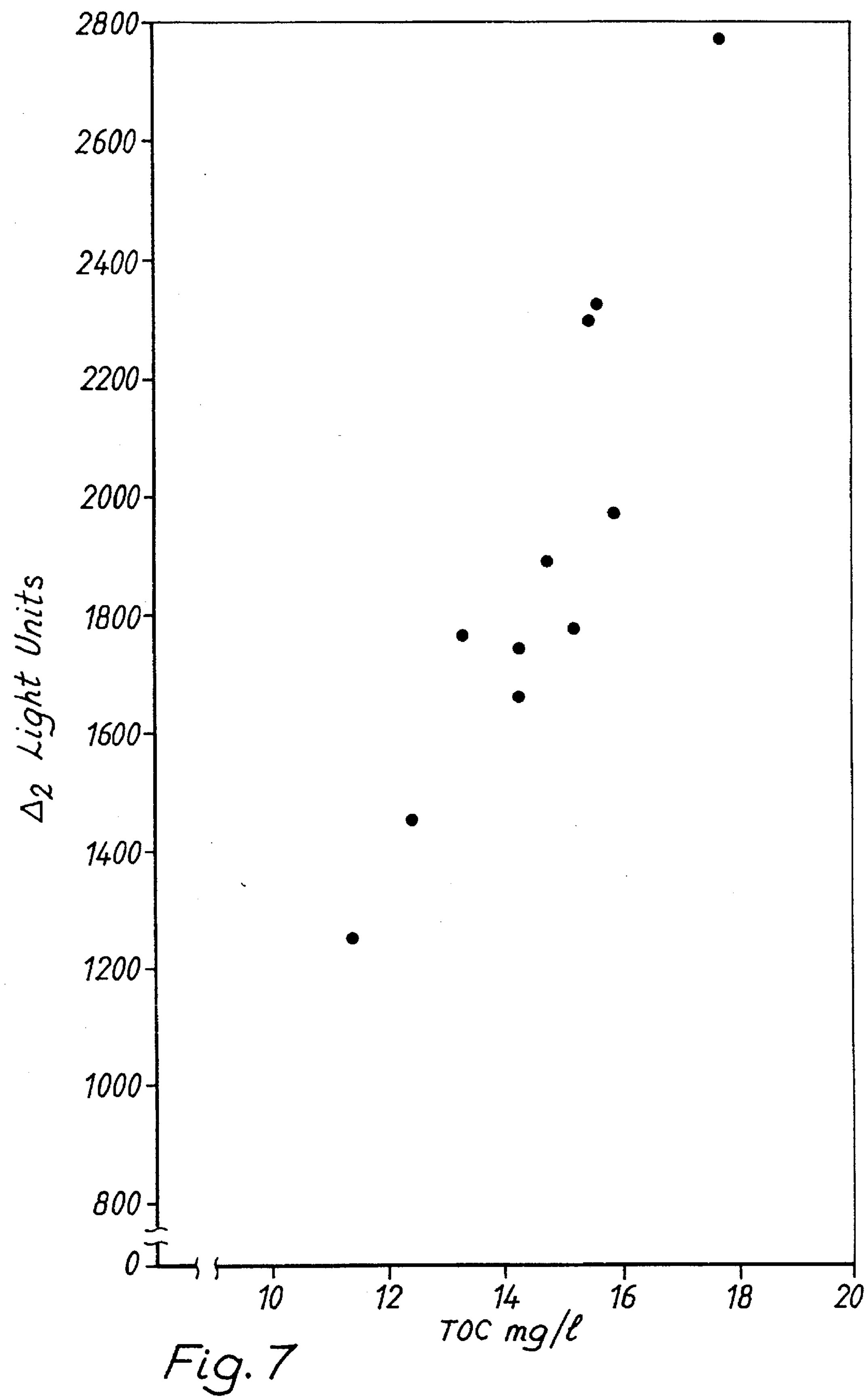
FIG. 7 is a correlation between the present invention and TOC.

A number of samples were taken from the River Winlap over a period of time. From each sample duplicate measurements were made of TOC and antioxidant capacity. FIG. 7 shows the correlation between antioxidant capacity ($\Delta_2$ on y-axis) and TOC (mg/l carbon x-axis). Each point is the mean of the duplicated samples. As is evident from the Figure, the two tests correlated well and this correlation was confirmed with tests at other sites.

We claim:

1. A method of assay of biological or chemical quality, in terms of antioxidant capacity, of a sample of water suspected to contain pollutants having an antioxidant capacity, which method comprises the steps of:

(1) carrying out a control, enzyme-catalyzed chemiluminescent action in a reaction mixture containing a chemical species starting material for said control reaction and measuring a level of chemiluminescence thereby generated;

(2) initiating and carrying out the same chemiluminescent reaction in the same reaction mixture to which said sample suspected to contain pollutants having an antioxidant capacity is added prior to or during said reaction, said chemiluminescent reaction generating a level of chemiluminescence whereby, when said sample is polluted, addition of said sample to said chemiluminescent reaction causes a reduction in said level of luminescence compared with the level of chemiluminescence generated by said control chemiluminescence reaction;

(3) monitoring said reduction in level of chemiluminescence, and (4) determining the water quality in terms of antioxidant capacity from said reduced level of chemiluminescence.

2. A method according to claim 1 wherein said reduced level of chemiluminescence is measured at a pre-determined time or during a predetermined time period or from the time period elapsed after initiation of the reaction or addition of the sample until a pre-determined reduced level of luminescence is obtained.

3. A method according to claim 1, in which the sample is added prior to initiation of said reaction, so that after initiation, the level of luminescence observed is reduced for a period of time, after which said level recovers to a substantially constant but still reduced level of luminescence and said reduction in the level of luminescence is measured after a pre-determined amount of time has elapsed from the time of initiation of the reaction, and is compared to a similar measurement of level of luminescence made on a said control reaction, the difference in level of luminescence between the sample and the control being an index of the antioxidant capacity of the sample.

4. A method according to claim 3, in which the time period from the time of initiation until the substantially constant level of luminescence is observed, is measured and wherein the measurement is an index of the antioxidant capacity of the sample.

5. A method according to claim 1, in which the sample is added to a progressing luminescent reaction.

6. A method according to claim 5, in which the luminescent reaction is carried out so that the level of luminescence rises to a plateau at which it remains substantially constant and said sample is added at said level or at a time when the level of luminescence is rising and is within 10% of reaching said substantially constant level, and said sample is added in an amount effective to cause a reduction in the level of luminescence, which is followed by a recovery to a substantially constant but still reduced level.

7. A method according to claim 6, in which the time interval between the time when the sample is added and a pre-determined level of recovery is measured.

8. A method according to claim 6, in which the level of recovery of luminescence at a given time interval from the time when the sample is added is measured and compared with the level of luminescence at the time when the sample was added.

9. A method according to claim 8 in which the level of recovery of luminescence is measured after a time interval from when the sample is added and compared with the level of luminescence of the control reaction after the same time interval.

10. A method of determining a change in biological or chemical quality, in terms of antioxidant capacity, of water suspected to contain pollutants having an antioxidant capacity, which method comprises the steps of:

carrying out a method of assay according to claim 1 on a sample of water;

removing specific antioxidant or particular classes of antioxidants from said water;

repeating the chemiluminescent reaction in the same reaction mixture, to which is added a sample of said water from which said antioxidant or antioxidants have been removed, thereby generating a new level of chemiluminescence and comparing the results of these two assays.

11. A method according to claim 1, in which the sample is sewage, river, sea water, reservoir, tap or industrial waste water.

12. A method according to claim 1, in which the chemiluminescent reaction is a peroxidase-catalyzed oxygen-dependent chemiluminescent reaction.

13. A method according to claim 12 in which the chemiluminescent reaction comprises the reaction of a peroxidase, an oxidant and a dihydrophthalazinedione (DPD) in the presence of an enhancer.

14. A method according to claim 13, in which the enhancer is para-iodophenol or para-hydroxycinnamic acid.

* * * * *